US008626271B2

(12) United States Patent
Dunki-Jacobs et al.

(10) Patent No.: US 8,626,271 B2
(45) Date of Patent: Jan. 7, 2014

(54) SYSTEM AND METHOD USING FLUORESCENCE TO EXAMINE WITHIN A PATIENT'S ANATOMY

(75) Inventors: Robert J. Dunki-Jacobs, Mason, OH (US); Youseph Yazdi, Princeton Junction, NJ (US); Michael P. Weir, Blanchester, OH (US); Paul G. Ritchie, Loveland, OH (US); David C. Youmans, Loveland, OH (US); Robert P. Gill, Mason, OH (US)

(73) Assignee: Ethicon Endo-Surgery, Inc., Cincinnati, OH (US)

( * ) Notice: Subject to any disclaimer, the term of this patent is extended or adjusted under 35 U.S.C. 154(b) by 1189 days.

(21) Appl. No.: 11/735,123

(22) Filed: Apr. 13, 2007

(65) Prior Publication Data

US 2008/0255458 A1    Oct. 16, 2008

(51) Int. Cl.
*A61B 6/00* (2006.01)

(52) U.S. Cl.
USPC ........... 600/476; 600/473; 600/424; 600/103; 600/117

(58) Field of Classification Search
USPC .......................................... 600/103, 117, 424
See application file for complete search history.

(56) References Cited

U.S. PATENT DOCUMENTS

| | | |
|---|---|---|
| 3,758,199 A | 9/1973 | Thaxter |
| 3,959,582 A | 5/1976 | Law et al. |
| 4,082,635 A | 4/1978 | Fritz et al. |
| 4,141,362 A | 2/1979 | Wurster |
| 4,313,431 A | 2/1982 | Frank |
| 4,379,039 A | 4/1983 | Fujimoto et al. |
| 4,403,273 A | 9/1983 | Nishioka |
| 4,409,477 A | 10/1983 | Carl |
| 4,421,382 A | 12/1983 | Doi et al. |
| 4,524,761 A | 6/1985 | Hattori et al. |
| 4,527,552 A | 7/1985 | Hattori |
| 4,573,465 A | 3/1986 | Sugiyama et al. |
| 4,576,999 A | 3/1986 | Eckberg |
| 4,597,380 A | 7/1986 | Raif et al. |

(Continued)

FOREIGN PATENT DOCUMENTS

| | | |
|---|---|---|
| DE | 3837248 | 5/1990 |
| EP | 1139141 | 10/2001 |

(Continued)

OTHER PUBLICATIONS

Kiang, M-H et al., "Surface-Micromachined Electrostatic-Comb Driven Scanning Micromirrors for Barcode Scanners" (date of first publication unknown).

(Continued)

*Primary Examiner* — Long V. Le
*Assistant Examiner* — Farshad Negarestan

(57) ABSTRACT

A system for examining an area of a patient's anatomy that comprises a probe capable of fluorescing, and a scanning beam assembly that scans the probe with a beam of excitation radiation and detects the probe's fluorescence. The scanning beam assembly including a radiation source capable of emitting one or more wavelengths of radiation that are capable of exciting the probe and causing the probe to fluoresce, a scanning device that directs the radiation onto a field-of-view to create a scan of the field-of-view, a detector to detect radiation returned from the field-of-view, and a controller to convert the detected radiation into a displayable fluorescence image.

29 Claims, 2 Drawing Sheets

(56) References Cited

U.S. PATENT DOCUMENTS

| | | | |
|---|---|---|---|
| 4,643,967 | A | 2/1987 | Bryant |
| 4,676,231 | A | 6/1987 | Hisazumi et al. |
| 4,760,840 | A | 8/1988 | Fournier, Jr. et al. |
| 4,803,550 | A | 2/1989 | Yabe et al. |
| 4,872,458 | A | 10/1989 | Kanehira et al. |
| 4,902,083 | A | 2/1990 | Wells |
| 4,902,115 | A | 2/1990 | Takahashi |
| 4,934,773 | A | 6/1990 | Becker |
| 4,938,205 | A | 7/1990 | Nudelman |
| 5,003,300 | A | 3/1991 | Wells |
| 5,023,905 | A | 6/1991 | Wells et al. |
| 5,048,077 | A | 9/1991 | Wells et al. |
| 5,074,860 | A | 12/1991 | Gregory et al. |
| 5,078,150 | A | 1/1992 | Hara et al. |
| 5,163,936 | A | 11/1992 | Black et al. |
| 5,163,945 | A | 11/1992 | Ortiz et al. |
| 5,172,685 | A | 12/1992 | Nudelman |
| 5,192,288 | A | 3/1993 | Thompson et al. |
| 5,200,819 | A | 4/1993 | Nudelman et al. |
| 5,200,838 | A | 4/1993 | Nudelman et al. |
| 5,207,670 | A | 5/1993 | Sinofsky |
| 5,218,195 | A | 6/1993 | Hakamata |
| 5,251,025 | A | 10/1993 | Cooper et al. |
| 5,251,613 | A * | 10/1993 | Adair ............ 600/109 |
| 5,269,289 | A | 12/1993 | Takehana et al. |
| 5,318,024 | A | 6/1994 | Kittrell et al. |
| 5,334,991 | A | 8/1994 | Wells et al. |
| 5,368,015 | A | 11/1994 | Wilk |
| 5,370,643 | A | 12/1994 | Krivoshlykov et al. |
| 5,387,197 | A | 2/1995 | Smith et al. |
| 5,393,647 | A | 2/1995 | Neukermans et al. |
| 5,436,655 | A | 7/1995 | Hiyama et al. |
| 5,467,104 | A | 11/1995 | Furness, III et al. |
| 5,488,862 | A | 2/1996 | Neukermans et al. |
| 5,531,740 | A | 7/1996 | Black |
| 5,545,211 | A | 8/1996 | An et al. |
| 5,552,452 | A | 9/1996 | Khadem et al. |
| 5,557,444 | A | 9/1996 | Melville et al. |
| 5,590,660 | A | 1/1997 | MacAulay et al. |
| 5,596,339 | A | 1/1997 | Furness, III et al. |
| 5,608,451 | A | 3/1997 | Konno et al. |
| 5,629,790 | A | 5/1997 | Neukermans et al. |
| 5,648,618 | A | 7/1997 | Neukermans et al. |
| 5,649,952 | A | 7/1997 | Lam |
| 5,657,165 | A | 8/1997 | Karpman et al. |
| 5,658,710 | A | 8/1997 | Neukermans |
| 5,659,327 | A | 8/1997 | Furness, III et al. |
| 5,694,237 | A | 12/1997 | Melville |
| 5,701,132 | A | 12/1997 | Kollin et al. |
| 5,713,891 | A | 2/1998 | Poppas |
| 5,728,121 | A | 3/1998 | Bimbo et al. |
| 5,735,792 | A | 4/1998 | Vanden Hoek et al. |
| 5,742,419 | A | 4/1998 | Dickensheets et al. |
| 5,742,421 | A | 4/1998 | Wells et al. |
| 5,751,465 | A | 5/1998 | Melville et al. |
| 5,768,461 | A | 6/1998 | Svetkoff et al. |
| 5,797,944 | A | 8/1998 | Nobles et al. |
| 5,817,061 | A | 10/1998 | Goodwin et al. |
| 5,823,943 | A | 10/1998 | Tomioka et al. |
| 5,827,176 | A | 10/1998 | Tanaka et al. |
| 5,827,190 | A | 10/1998 | Palcic et al. |
| 5,841,553 | A | 11/1998 | Neukermans |
| 5,861,549 | A | 1/1999 | Neukermans et al. |
| 5,867,297 | A | 2/1999 | Kiang et al. |
| 5,895,866 | A | 4/1999 | Neukermans et al. |
| 5,903,397 | A | 5/1999 | Melville et al. |
| 5,907,425 | A | 5/1999 | Dickensheets et al. |
| 5,913,591 | A | 6/1999 | Melville |
| 5,947,930 | A | 9/1999 | Schwemberger et al. |
| 5,969,465 | A | 10/1999 | Neukermans et al. |
| 5,969,871 | A | 10/1999 | Tidwell et al. |
| 5,982,528 | A | 11/1999 | Melville |
| 5,982,555 | A | 11/1999 | Melville et al. |
| 5,993,037 | A | 11/1999 | Tomioka et al. |
| 5,995,264 | A | 11/1999 | Melville |
| 6,007,208 | A | 12/1999 | Dickensheets et al. |
| 6,008,781 | A | 12/1999 | Furness, III et al. |
| 6,013,025 | A | 1/2000 | Bonne et al. |
| 6,016,440 | A | 1/2000 | Simon et al. |
| 6,017,356 | A | 1/2000 | Frederick et al. |
| 6,017,603 | A | 1/2000 | Tokuda et al. |
| 6,024,744 | A | 2/2000 | Kese et al. |
| 6,043,799 | A | 3/2000 | Tidwell |
| 6,044,705 | A | 4/2000 | Neukermans et al. |
| 6,046,720 | A | 4/2000 | Melville et al. |
| 6,049,407 | A | 4/2000 | Melville |
| 6,056,721 | A | 5/2000 | Shulze |
| 6,057,952 | A | 5/2000 | Kubo et al. |
| 6,059,720 | A | 5/2000 | Furusawa et al. |
| 6,061,163 | A | 5/2000 | Melville |
| 6,064,779 | A | 5/2000 | Neukermans et al. |
| 6,069,725 | A | 5/2000 | Melville |
| 6,086,528 | A | 7/2000 | Adair |
| 6,086,531 | A | 7/2000 | Tomioka et al. |
| 6,088,145 | A | 7/2000 | Dickensheets et al. |
| 6,097,353 | A | 8/2000 | Melville et al. |
| 6,122,394 | A | 9/2000 | Neukermans et al. |
| 6,139,175 | A | 10/2000 | Tomioka et al. |
| 6,140,979 | A | 10/2000 | Gerhard et al. |
| 6,151,167 | A | 11/2000 | Melville |
| 6,154,305 | A | 11/2000 | Dickensheets et al. |
| 6,154,321 | A | 11/2000 | Melville et al. |
| 6,157,352 | A | 12/2000 | Kollin et al. |
| 6,166,841 | A | 12/2000 | Melville |
| 6,172,789 | B1 | 1/2001 | Kino et al. |
| 6,178,346 | B1 | 1/2001 | Amundson et al. |
| 6,179,776 | B1 | 1/2001 | Adams et al. |
| 6,191,761 | B1 | 2/2001 | Melville et al. |
| 6,192,267 | B1 * | 2/2001 | Scherninski et al. ......... 600/473 |
| 6,200,595 | B1 | 3/2001 | Motoyashiki et al. |
| 6,204,829 | B1 | 3/2001 | Tidwell |
| 6,204,832 | B1 | 3/2001 | Melville et al. |
| 6,207,392 | B1 | 3/2001 | Weiss et al. |
| 6,210,401 | B1 | 4/2001 | Lai |
| 6,220,711 | B1 | 4/2001 | Melville |
| 6,221,068 | B1 | 4/2001 | Fried et al. |
| 6,229,139 | B1 | 5/2001 | Neukermans et al. |
| 6,235,017 | B1 | 5/2001 | Jegorov et al. |
| 6,243,186 | B1 | 6/2001 | Melville |
| 6,245,590 | B1 | 6/2001 | Wine et al. |
| 6,256,131 | B1 | 7/2001 | Wine et al. |
| 6,257,727 | B1 | 7/2001 | Melville |
| 6,272,907 | B1 | 8/2001 | Neukermans et al. |
| 6,276,798 | B1 | 8/2001 | Gil et al. |
| 6,281,862 | B1 | 8/2001 | Tidwell et al. |
| 6,284,185 | B1 | 9/2001 | Tokuda et al. |
| 6,285,489 | B1 | 9/2001 | Helsel et al. |
| 6,285,505 | B1 | 9/2001 | Melville et al. |
| 6,288,816 | B1 | 9/2001 | Melville et al. |
| 6,292,287 | B1 | 9/2001 | Fujinoki |
| 6,293,911 | B1 | 9/2001 | Imaizumi et al. |
| 6,294,239 | B1 | 9/2001 | Tokuda et al. |
| 6,294,775 | B1 | 9/2001 | Seibel et al. |
| 6,317,103 | B1 | 11/2001 | Furness, III et al. |
| 6,323,037 | B1 | 11/2001 | Lauto et al. |
| 6,324,007 | B1 | 11/2001 | Melville |
| 6,327,493 | B1 | 12/2001 | Ozawa et al. |
| 6,331,909 | B1 | 12/2001 | Dunfield |
| 6,333,110 | B1 | 12/2001 | Barbera-Guillem |
| 6,338,641 | B2 | 1/2002 | Nicholls |
| 6,352,344 | B2 | 3/2002 | Tidwell |
| 6,353,183 | B1 | 3/2002 | Ott et al. |
| 6,362,912 | B1 | 3/2002 | Lewis et al. |
| 6,364,829 | B1 | 4/2002 | Fulghum |
| 6,369,928 | B1 | 4/2002 | Mandella et al. |
| 6,369,953 | B2 | 4/2002 | Melville et al. |
| 6,369,954 | B1 | 4/2002 | Berge et al. |
| 6,370,406 | B1 | 4/2002 | Wach et al. |
| 6,370,422 | B1 | 4/2002 | Richards-Kortum et al. |
| 6,373,995 | B1 | 4/2002 | Moore |
| 6,384,406 | B1 | 5/2002 | Wine et al. |
| 6,388,641 | B2 | 5/2002 | Tidwell et al. |
| 6,392,220 | B1 | 5/2002 | Slater et al. |
| 6,396,461 | B1 | 5/2002 | Lewis et al. |

(56) References Cited

U.S. PATENT DOCUMENTS

| | | | |
|---|---|---|---|
| 6,414,779 B1 | 7/2002 | Mandella et al. |
| 6,417,502 B1 | 7/2002 | Stoner et al. |
| 6,423,956 B1 | 7/2002 | Mandella et al. |
| 6,425,900 B1 | 7/2002 | Knodel et al. |
| 6,426,013 B1 | 7/2002 | Neukermans et al. |
| 6,433,907 B1 | 8/2002 | Lippert et al. |
| 6,435,637 B1 | 8/2002 | Lyman |
| 6,441,356 B1 | 8/2002 | Mandella et al. |
| 6,445,362 B1 | 9/2002 | Tegreene |
| 6,447,524 B1 | 9/2002 | Knodel et al. |
| 6,462,770 B1 | 10/2002 | Cline et al. |
| 6,464,363 B1 | 10/2002 | Nishioka et al. |
| 6,467,345 B1 | 10/2002 | Neukermans et al. |
| 6,470,124 B1 | 10/2002 | Le Gargasson et al. |
| 6,477,403 B1 | 11/2002 | Eguchi et al. |
| 6,478,809 B1 | 11/2002 | Brotz |
| 6,485,413 B1 | 11/2002 | Boppart |
| 6,492,962 B2 | 12/2002 | Melville et al. |
| 6,494,578 B1 | 12/2002 | Plummer et al. |
| 6,498,941 B1 * | 12/2002 | Jackson ...................... 600/310 |
| 6,503,196 B1 | 1/2003 | Kehr et al. |
| 6,510,338 B1 | 1/2003 | Irion et al. |
| 6,512,622 B2 | 1/2003 | Wine et al. |
| 6,513,939 B1 | 2/2003 | Fettig et al. |
| 6,515,278 B2 | 2/2003 | Wine et al. |
| 6,515,781 B2 | 2/2003 | Lewis et al. |
| 6,520,972 B2 | 2/2003 | Peters |
| 6,522,444 B2 | 2/2003 | Mandella et al. |
| 6,525,310 B2 | 2/2003 | Dunfield |
| 6,527,708 B1 | 3/2003 | Nakamura et al. |
| 6,529,770 B1 | 3/2003 | Grimblatov |
| 6,530,698 B1 | 3/2003 | Kuhara et al. |
| 6,535,183 B2 | 3/2003 | Melville et al. |
| 6,535,325 B2 | 3/2003 | Helsel et al. |
| 6,537,211 B1 | 3/2003 | Wang et al. |
| 6,538,625 B2 | 3/2003 | Tidwell et al. |
| 6,545,260 B1 | 4/2003 | Katashiro et al. |
| 6,560,028 B2 | 5/2003 | Melville et al. |
| 6,563,105 B2 | 5/2003 | Seibel et al. |
| 6,563,106 B2 | 5/2003 | Bowers et al. |
| 6,572,606 B2 | 6/2003 | Kliewer et al. |
| 6,583,117 B2 | 6/2003 | Owen et al. |
| 6,583,772 B1 | 6/2003 | Lewis et al. |
| 6,585,642 B2 | 7/2003 | Christopher |
| 6,603,552 B1 | 8/2003 | Cline et al. |
| 6,608,297 B2 | 8/2003 | Neukermans et al. |
| 6,639,570 B2 | 10/2003 | Furness, III et al. |
| 6,639,719 B2 | 10/2003 | Tegreene et al. |
| 6,650,877 B1 | 11/2003 | Tarbouriech et al. |
| 6,653,621 B2 | 11/2003 | Wine et al. |
| 6,654,158 B2 | 11/2003 | Helsel et al. |
| 6,661,393 B2 | 12/2003 | Tegreene et al. |
| 6,674,993 B1 | 1/2004 | Tarbouriech |
| 6,685,804 B1 | 2/2004 | Ikeda et al. |
| 6,687,034 B2 | 2/2004 | Wine et al. |
| 6,689,056 B1 | 2/2004 | Kilcoyne et al. |
| 6,699,170 B1 | 3/2004 | Crocker et al. |
| 6,700,552 B2 | 3/2004 | Kollin et al. |
| 6,714,331 B2 | 3/2004 | Lewis et al. |
| 6,734,835 B2 | 5/2004 | Tidwell et al. |
| 6,736,511 B2 | 5/2004 | Plummer et al. |
| 6,741,884 B1 | 5/2004 | Freeman et al. |
| 6,749,346 B1 | 6/2004 | Dickensheets et al. |
| 6,755,536 B2 | 6/2004 | Tegreene et al. |
| 6,762,867 B2 | 7/2004 | Lippert et al. |
| 6,768,588 B2 | 7/2004 | Urey |
| 6,771,001 B2 | 8/2004 | Mao et al. |
| 6,782,748 B2 | 8/2004 | Weber et al. |
| 6,786,382 B1 | 9/2004 | Hoffman |
| 6,795,221 B1 | 9/2004 | Urey |
| 6,802,809 B2 | 10/2004 | Okada |
| 6,803,561 B2 | 10/2004 | Dunfield |
| 6,821,245 B2 | 11/2004 | Cline et al. |
| 6,826,424 B1 * | 11/2004 | Zeng et al. ...................... 600/476 |
| 6,845,190 B1 | 1/2005 | Smithwick et al. |
| 6,856,436 B2 | 2/2005 | Brukilacchio et al. |
| 6,856,712 B2 | 2/2005 | Fauver et al. |
| 6,879,428 B2 | 4/2005 | Massieu |
| 6,888,552 B2 | 5/2005 | Debevec et al. |
| 6,894,823 B2 | 5/2005 | Taylor et al. |
| 6,899,675 B2 | 5/2005 | Cline et al. |
| 6,902,527 B1 | 6/2005 | Doguchi et al. |
| 6,905,057 B2 | 6/2005 | Swayze et al. |
| 6,939,364 B1 | 9/2005 | Soltz et al. |
| 6,957,898 B2 | 10/2005 | Yu |
| 6,967,757 B1 | 11/2005 | Allen et al. |
| 6,974,472 B2 | 12/2005 | Hong et al. |
| 6,975,898 B2 | 12/2005 | Seibel et al. |
| 6,976,994 B2 | 12/2005 | Ballou et al. |
| 6,978,921 B2 | 12/2005 | Shelton, IV et al. |
| 6,985,271 B2 | 1/2006 | Yazdi et al. |
| 6,991,602 B2 | 1/2006 | Nakazawa et al. |
| 7,005,195 B2 | 2/2006 | Cheng et al. |
| 7,009,634 B2 | 3/2006 | Iddan et al. |
| 7,013,730 B2 | 3/2006 | Malametz |
| 7,015,956 B2 | 3/2006 | Luo et al. |
| 7,018,401 B1 | 3/2006 | Hyodoh et al. |
| 7,023,402 B2 | 4/2006 | Lewis et al. |
| 7,025,777 B2 | 4/2006 | Moore |
| 7,033,348 B2 | 4/2006 | Alfano et al. |
| 7,035,299 B2 * | 4/2006 | Hori et al. ...................... 372/26 |
| 7,035,777 B2 | 4/2006 | Araki et al. |
| 7,061,450 B2 | 6/2006 | Bright et al. |
| 7,065,301 B2 | 6/2006 | Shastri et al. |
| 7,066,879 B2 | 6/2006 | Fowler et al. |
| 7,071,594 B1 | 7/2006 | Yan et al. |
| 7,071,931 B2 | 7/2006 | Tegreene et al. |
| 7,078,378 B1 | 7/2006 | Owen et al. |
| 7,108,656 B2 | 9/2006 | Fujikawa et al. |
| 7,112,302 B2 | 9/2006 | Yoshimi et al. |
| 7,126,903 B2 | 10/2006 | Feenstra et al. |
| 7,189,961 B2 | 3/2007 | Johnston et al. |
| 7,190,329 B2 | 3/2007 | Lewis et al. |
| 7,232,071 B2 | 6/2007 | Lewis et al. |
| 7,271,383 B2 | 9/2007 | Chee |
| 7,391,013 B2 | 6/2008 | Johnston et al. |
| 2001/0055462 A1 | 12/2001 | Seibel |
| 2002/0015724 A1 | 2/2002 | Yang et al. |
| 2002/0024495 A1 | 2/2002 | Lippert et al. |
| 2002/0050956 A1 | 5/2002 | Gerhard et al. |
| 2002/0075284 A1 | 6/2002 | Rabb, III |
| 2002/0088925 A1 | 7/2002 | Nestorovic et al. |
| 2002/0115922 A1 * | 8/2002 | Waner et al. ...................... 600/407 |
| 2002/0141026 A1 | 10/2002 | Wiklof et al. |
| 2002/0158814 A1 | 10/2002 | Bright et al. |
| 2002/0163484 A1 | 11/2002 | Furness, III et al. |
| 2002/0167462 A1 | 11/2002 | Lewis et al. |
| 2002/0171776 A1 | 11/2002 | Tegreene et al. |
| 2002/0171937 A1 | 11/2002 | Tegreene et al. |
| 2003/0016187 A1 | 1/2003 | Melville et al. |
| 2003/0030753 A1 | 2/2003 | Kondo et al. |
| 2003/0032143 A1 | 2/2003 | Neff et al. |
| 2003/0034709 A1 | 2/2003 | Jerman |
| 2003/0058190 A1 | 3/2003 | Lewis et al. |
| 2003/0086172 A1 | 5/2003 | Urey |
| 2003/0092995 A1 | 5/2003 | Thompson |
| 2003/0130562 A1 | 7/2003 | Barbato et al. |
| 2003/0142934 A1 | 7/2003 | Pan et al. |
| 2003/0159447 A1 | 8/2003 | Sergio et al. |
| 2003/0214460 A1 | 11/2003 | Kovacs |
| 2003/0216729 A1 | 11/2003 | Marchitto et al. |
| 2004/0004585 A1 | 1/2004 | Brown et al. |
| 2004/0057103 A1 | 3/2004 | Bernstein |
| 2004/0075624 A1 | 4/2004 | Tegreene et al. |
| 2004/0076390 A1 | 4/2004 | Dong Yang et al. |
| 2004/0085261 A1 | 5/2004 | Lewis et al. |
| 2004/0085617 A1 | 5/2004 | Helsel et al. |
| 2004/0087844 A1 | 5/2004 | Yen |
| 2004/0101822 A1 * | 5/2004 | Wiesner et al. ...................... 435/5 |
| 2004/0113059 A1 | 6/2004 | Kawano et al. |
| 2004/0118821 A1 | 6/2004 | Han et al. |
| 2004/0119004 A1 | 6/2004 | Wine et al. |
| 2004/0122328 A1 | 6/2004 | Wang et al. |
| 2004/0133786 A1 | 7/2004 | Tarbouriech |

(56) References Cited

U.S. PATENT DOCUMENTS

| | | |
|---|---|---|
| 2004/0151466 A1 | 8/2004 | Crossman-Bosworth et al. |
| 2004/0155186 A1 | 8/2004 | Nestorovic et al. |
| 2004/0155834 A1 | 8/2004 | Wit et al. |
| 2004/0179254 A1 | 9/2004 | Lewis et al. |
| 2004/0186351 A1* | 9/2004 | Imaizumi et al. ............ 600/160 |
| 2004/0196518 A1 | 10/2004 | Wine et al. |
| 2004/0223202 A1 | 11/2004 | Lippert et al. |
| 2004/0225222 A1 | 11/2004 | Zeng et al. |
| 2004/0236371 A1 | 11/2004 | McNally-Heintzelman et al. |
| 2004/0240866 A1 | 12/2004 | Ramsbottom |
| 2004/0252377 A1 | 12/2004 | Urey |
| 2004/0254474 A1 | 12/2004 | Seibel et al. |
| 2005/0010787 A1 | 1/2005 | Tarbouriech |
| 2005/0014995 A1 | 1/2005 | Amundson et al. |
| 2005/0020877 A1 | 1/2005 | Ishihara et al. |
| 2005/0020926 A1 | 1/2005 | Wiklof et al. |
| 2005/0023356 A1 | 2/2005 | Wiklof et al. |
| 2005/0030305 A1 | 2/2005 | Brown et al. |
| 2005/0038322 A1 | 2/2005 | Banik |
| 2005/0116038 A1 | 6/2005 | Lewis et al. |
| 2005/0162762 A1 | 7/2005 | Novak |
| 2005/0187441 A1 | 8/2005 | Kawasaki et al. |
| 2005/0203343 A1 | 9/2005 | Kang et al. |
| 2005/0240147 A1 | 10/2005 | Makower et al. |
| 2006/0010985 A1 | 1/2006 | Schneider |
| 2006/0084867 A1 | 4/2006 | Tremblay et al. |
| 2006/0164330 A1 | 7/2006 | Bright et al. |
| 2006/0183246 A1 | 8/2006 | Wiesner et al. |
| 2006/0195014 A1 | 8/2006 | Seibel et al. |
| 2006/0238774 A1 | 10/2006 | Lindner et al. |
| 2006/0245971 A1 | 11/2006 | Burns et al. |
| 2006/0284790 A1 | 12/2006 | Tegreene et al. |
| 2007/0038119 A1 | 2/2007 | Chen et al. |
| 2007/0046778 A1 | 3/2007 | Ishihara et al. |
| 2007/0135770 A1 | 6/2007 | Hunt et al. |
| 2007/0156021 A1 | 7/2007 | Morse et al. |
| 2007/0161876 A1 | 7/2007 | Bambot et al. |
| 2007/0162093 A1 | 7/2007 | Porter et al. |
| 2007/0167681 A1 | 7/2007 | Gill et al. |
| 2007/0173707 A1 | 7/2007 | Mitra |
| 2007/0179366 A1 | 8/2007 | Pewzner et al. |
| 2007/0197874 A1 | 8/2007 | Ishihara |
| 2007/0197875 A1 | 8/2007 | Osaka |
| 2007/0203413 A1 | 8/2007 | Frangioni |
| 2007/0213588 A1 | 9/2007 | Morishita et al. |
| 2007/0213618 A1 | 9/2007 | Li et al. |
| 2007/0225695 A1 | 9/2007 | Mayer et al. |
| 2007/0238930 A1 | 10/2007 | Wiklof et al. |
| 2007/0244365 A1 | 10/2007 | Wiklof |
| 2007/0260121 A1 | 11/2007 | Bakos et al. |
| 2007/0260273 A1 | 11/2007 | Cropper et al. |
| 2008/0058629 A1 | 3/2008 | Seibel et al. |

FOREIGN PATENT DOCUMENTS

| | | |
|---|---|---|
| EP | 1716802 | 11/2006 |
| EP | 1747751 | 1/2007 |
| EP | 1797813 | 6/2007 |
| JP | 2007-244590 | 9/2007 |
| JP | 2007-244680 | 9/2007 |
| WO | WO 98/13720 | 4/1998 |
| WO | WO 99/18456 | 4/1999 |
| WO | 99/58930 | 11/1999 |
| WO | 00/13210 | 3/2000 |
| WO | 01/10322 | 2/2001 |
| WO | 01/60274 | 8/2001 |
| WO | 02/062239 | 8/2002 |
| WO | WO 03/069380 | 8/2003 |
| WO | 03/088643 | 10/2003 |
| WO | 03/098918 | 11/2003 |
| WO | 03/101287 | 11/2003 |
| WO | 2006/020605 | 2/2006 |
| WO | WO 2006/049787 | 5/2006 |
| WO | WO 2006/055733 | 5/2006 |
| WO | 2007/041542 | 4/2007 |
| WO | 2007/070831 | 6/2007 |
| WO | WO 2007/067163 | 6/2007 |
| WO | WO 2007/084915 | 7/2007 |

OTHER PUBLICATIONS

Lewis, J.R. et al., "Scanned beam medical imager," MOEMS Display and Imaging Systems II, Proceedings of SPIE vol. 5348, pp. 40-51 (2004).

James, R. et al., "Update on MEMS-based Scanned Beam Imager" (date of first publication unknown).

Wiklof, C., "Display technology spawns laser camera," Laser Focus World (Dec. 2004).

"Press Information—Phillips' Fluid Lenses Bring Things into Focus," http://www.newscenter.philips.com (Mar. 3, 2004).

Lettice, J., "The $5 'no moving parts' fluid zoom lens—twice," The Register (Mar. 15, 2004).

"Volcano Products—IVUS Imaging Visions® PV018," http://www.volcanotherapeutics.com (date of first publication unknown).

Barhoum, E.S. et al., "Optical modeling of an ultrathin scanning fiber endoscope, a preliminary study of confocal versus non-confocal detection," Optics Express, vol. 13, No. 19, pp. 7548-7652 (Sep. 19, 2005).

"Crystalplex Technology—PlxBead™ Superior Qualities," http:www.crystalplex.com (date of first publication unknown).

"Microvision [illuminating information] Products/Overview, Corporate Overview Presentation 2006" (2006).

"Holographic Beam Combiner for Ladar, Printer, Fiber Optics, and Cancer Treatment," by Digital Optics Technologies, Inc., http://www.mdatechnology.net (date of first publication unknown).

Brown, D.M., Abstract from SPIE Digital Library for "High-power laser diode beam combiner," Optical Engineering, vol. 42, Issue 11 (2003).

Literature entitled "All fiber beam combiner from Point Source" (Oct. 13, 2006).

"Custom Polarzing Cube Beamsplitters," from GlobalSpec The Engineering Search Engine, http://www.globalspec.com (date of first publication unknown).

Literature entitled "Dallas Semiconductor MAXIM—Visible-Laser Driver has Digitally Controlled Power Modulation," by Maxim Integrated Products, http://www.maxim-ic.com (Jul. 1, 2001).

"SCAN Mode Strategies for SCUBA-2" (May 25, 2005).

Seifert, M. et al., "High Power Diode Laser Beam Scanning in Multi-Kilowatt Range," Proceedings of the 23rd International Congress on Applications of Lasers and Electro-Optics (2004).

Jutzi, B. et al., "Sub-Pixel Edge Localization Based on Laser Waveform Analysis," ISPRS WG III/3, III/4, V/3 Workshop "Laser scanning 2005," Enschede, the Netherlands (Sep. 12-14, 2005).

"Bladeless Trocars," by Johnson & Johnson, http://www.jnjgateway.com (date of first publication unknown).

Yeh, R. et al., "Microelectromechanical Components for Articulated Microrobots" (date of first publication unknown).

Xu, Q. et al., "Micrometre-scale silicon electro-optic modulator," Nature, vol. 435, pp. 325-327 (May 19, 2005).

Park, H. et al., "Development of Double-Sided Silicon Strip Position Sensor," 2005 IEEE Nuclear Science Symposium Conference Record, pp. 781-785 (2005).

Hammond, S.W., "Architecture and Operation of a Systolic Sparse Matrix Engine," Proceedings of the 3rd SIAM Conference on Parallel Processing for Scientific Computing, pp. 419-423 (1987).

Ra, H. et al., "Biomedical Optics & Medical Imaging—Microtechnology enables endoscopic confocal microscopy," SPIE (http://spie.org) (2007).

Invitation to Pay Additional Fees with Partial International Search Report, PCT/US2008/074275 (Jan. 16, 2009).

Invitation to Pay Additional Fees with Partial International Search Report, PCT/US2008/074273 (Dec. 30, 2008).

International Search Report issued regarding International Application No. PCT/US2007/078868 (Mar. 28, 2008).

PCT, International Search Report, PCT/US2008/056589 (Jul. 30, 2008).

(56) References Cited

OTHER PUBLICATIONS

PCT, International Search Report, PCT/US2008/059231 (Jul. 4, 2008).
PCT, International Search Report, PCT/US2007/087923 (May 21, 2008).
PCT, International Search Report, PCT/US2008/056596 (Jun. 23, 2008).
PCT, International Search Report, PCT/US2008/059235 (Jul. 14, 2008).
PCT, International Search Report, PCT/US2007/087930 (Jul. 3, 2008).
PCT, International Search Report, PCT/US2008/051274 (Jul. 18, 2008).
Barhoum, E.S. et al., "Optical Modeling of an Ultrathin Scanning Fiber Endoscope, a Preliminary Study of Confocal Versus Non-Confocal Detection," Optics Express, vol. 13, No. 19 (Sep. 2005).
PCT, International Search Report, PCT/US2008/066552 (Oct. 23, 2008).

* cited by examiner

SYSTEM AND METHOD USING FLUORESCENCE TO EXAMINE WITHIN A PATIENT'S ANATOMY

FIELD OF THE INVENTION

The present invention is related generally to imaging fluorescence in the anatomy, and more particularly to medical applications of fluorescent imaging of the anatomy using a scanning beam assembly.

BACKGROUND OF THE INVENTION

U.S. Published Application 2005/0020926 discloses a scanning beam imager (SBI) which is reproduced in FIG. 1 herein. This imager can be used in applications in which cameras have been used in the past. In particular it can be used in medical devices such as video endoscopes, laparoscopes, etc.

FIG. 1 shows a block diagram of one example of a scanned beam imager 102. An illuminator 104, which is part of a variable illuminator 109, creates a first beam of light 106. A scanner 108 deflects the first beam of light across a field-of-view (FOV) 111 to produce a second scanned beam of light 110, shown in two positions 110a and 110b. The scanned beam of light 110 sequentially illuminates spots 112 in the FOV 111, shown as positions 112a and 112b, corresponding to beam positions 110a and 110b, respectively. While the beam 110 illuminates the spots 112, the illuminating light beam 110 is reflected, absorbed, scattered, refracted, or otherwise affected by the object or material in the FOV 111 to produce scattered light energy. A portion of the scattered light energy 114, shown emanating from spot positions 112a and 112b as scattered energy rays 114a and 114b, respectively, travels to one or more detectors 116 that receive the light and produce electrical signals corresponding to the amount of light energy received. Image information is provided as an array of data, where each location in the array corresponds to a position in the scan pattern. The electrical signals drive a controller 118 that builds up a digital image and transmits it for further processing, decoding, archiving, printing, display, or other treatment or use via interface 120.

Illuminator 104 may include multiple emitters such as, for instance, light emitting diodes (LEDs), lasers, thermal sources, arc sources, fluorescent sources, gas discharge sources, or other types of illuminators. In some embodiments, illuminator 104 comprises a red laser diode having a wavelength of approximately 635 to 670 nanometers (nm). In another embodiment, illuminator 104 comprises three lasers: a red diode laser, a green diode-pumped solid state (DPSS) laser, and a blue DPSS laser at approximately 635 nm, 532 nm, and 473 nm, respectively. Light source 104 may include, in the case of multiple emitters, beam combining optics to combine some or all of the emitters into a single beam. Light source 104 may also include beam-shaping optics such as one or more collimating lenses and/or apertures. Additionally, while the wavelengths described in the previous embodiments have been in the optically visible range, other wavelengths may be within the scope of the invention. Light beam 106, while illustrated as a single beam, may comprise a plurality of beams converging on a single scanner 108 or onto separate scanners 108.

One example of these scanners employs a MEMS scanner capable of deflection about two orthogonal scan axes, in which both scan axes are driven at a frequency near their natural mechanical resonant frequency of the MEMS device upon which it is constructed. In another example, one axis is operated near resonance while the other is operated substantially off resonance. For completeness it is also noted that scanners are also know that employ two reflectors, one of which oscillates sinusoidally and the other of which simply scans linearly.

Scanning beam imagers are advantageous because they are often able to provide higher resolution and a broader scan area. The SBI is able to provide pixel by pixel interrogation with a high range of data capture. However, even with a SBI there are some the anatomy structures within the anatomy that are difficult to examine, like the biliary tree, colon, and the gastrointestinal tract. The SBI can be adapted, as in the present invention, for use in fluorescent imaging to visualize the anatomy or an instrument that is fluorescing due to the presence of a fluorescent probe or fluorophore. Provided herein is a system that is an improvement in fluorescent imaging of the anatomy; a system that is capable of visualizing the biliary tree during a cholecystectomy or cancer cells during a colorectal cancer resection or lumpectomy, or ureters during a colorectal or gynecological procedure.

SUMMARY OF THE INVENTION

In one aspect, the present invention provides a system for examining an area of a patient's anatomy that comprises a probe capable of fluorescing, and a scanning beam assembly that scans the probe with a beam of excitation radiation and detects the probe's fluorescence. The scanning beam assembly comprises a radiation source capable of emitting one or more wavelengths of radiation that are capable of exciting the probe and causing the probe to fluoresce, a scanning device that directs the radiation onto a field-of-view to create a scan of the field-of-view, a detector to detect radiation returned from the field-of-view, and a controller to convert the detected radiation into a displayable fluorescence image. In another embodiment, the radiation source emits at least one wavelength of radiation to image the field-of-view. The displayable image of the fluorescence is anatomically registered to the image of the field-of-view when displayed.

In another aspect, the present invention provides a method for observing fluorescence within an area of a patient's anatomy that comprises delivering a probe capable of fluorescing into patient's anatomy, introducing at least part of a scanning beam assembly into the anatomy to scan the area of the anatomy including the probe, exciting the probe, detecting the probe's fluorescence, and converting the probe's fluorescence into a displayable image of the fluorescence within the area of the anatomy including the probe. The scanning beam assembly comprises a radiation source capable of emitting one or more wavelengths of radiation that are capable of exciting the probe and causing the probe to fluoresce, a scanning device that directs the radiation onto the area of the anatomy to create a scan of the area; a detector to detect radiation returned from the area of the anatomy, and a controller to convert the detected radiation into a displayable fluorescence image.

In another aspect, the present invention provides a method of observing an area of a patient's anatomy that comprises delivering a probe capable of fluorescing to an area of patient's anatomy, introducing an instrument including at least in part a fluorophore, exposing the probe and the fluorophore to one or more wavelengths of radiation capable of exciting the probe, fluorophore, or both into fluorescing, detecting the fluorescence of the probe, fluorophore, or both, converting the detected fluorescence of the probe and fluorophore into a fluorescence image that can be displayed, and displaying the fluorescence image on a display system that is capable of displaying a combined image.

In another aspect, the present invention provides a method for examining an area of a patient's anatomy that comprises introducing at least part of a scanning beam assembly into the anatomy to scan the anatomy, scanning the anatomy with a wavelength of radiation that is capable of exciting naturally occurring autofluorescent cell constituents, detecting the cell constituents fluorescence, and converting the fluorescence into a displayable fluorescence image. The scanning beam assembly including a radiation source capable of emitting one or more wavelengths of radiation that are capable of exciting the probe and causing the probe to fluoresce, a scanning device that directs the radiation onto a field-of-view, a detector to detect radiation returned from the field-of-view, and a controller to convert the detected radiation into a displayable fluorescence image.

The scanning beam assembly has an optical pathway that is largely a single optical fiber that can transmit a combined beam of radiation along its length. This optical architecture has the advantage of allowing a large amount of imaging radiation, excitation radiation, or both to be delivered to a small region (e.g., a single pixel) using a low-power source. The result is high radiation intensity which provides a significant improvement in the signal to noise ratio and photosensitivity for fluorescent imaging.

DETAILED DESCRIPTION OF THE INVENTION

Figure 1:
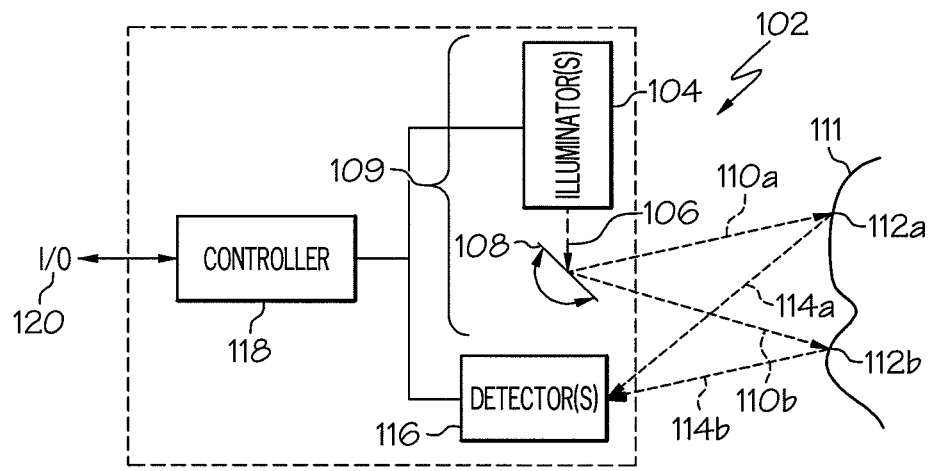
FIG. 1 is a schematic illustration of a scanning beam imager known in the art from U.S. Published Application 2005/0020926.

Before explaining the several embodiments of the present invention in detail, it should be noted that each embodiment is not limited in its application or use to the details of construction and arrangement of parts and steps illustrated in the accompanying drawings and description. The illustrative embodiments of the invention may be implemented or incorporated in other embodiments, variations and modifications, and may be practiced or carried out in various ways. Furthermore, unless otherwise indicated, the terms and expressions employed herein have been chosen for the purpose of describing the illustrative embodiments of the present invention for the convenience of the reader and are not for the purpose of limiting the invention.

It is further understood that any one or more of the following-described embodiments and examples can be combined with any one or more of the other following-described embodiments or examples.

In one embodiment, the present invention provides a system for examining an area of a patient's anatomy. The system comprises a probe capable of fluorescing and a scanning beam assembly that scans the probe with a beam of excitation radiation and detects the probe's fluorescence. The scanning beam assembly comprises a radiation source capable of emitting one or more wavelengths of radiation that are capable of exciting the probe and causing the probe to fluoresce, a reflector that receives the radiation from the radiation source to direct the radiation onto a field-of-view, wherein the reflector oscillates in at least two directions to create a scan of the field-of-view, at least one detector to detect radiation returned from the field-of-view, and a controller to convert the detected radiation into a displayable image of the fluorescence within the field-of-view.

Fluorescence is an optical phenomenon that occurs when radiation is absorbed and excites electrons to a higher energy level, and then nearly instantaneously the electrons move from the excited energy level to a lower energy level, which causes the material to emit radiation at a longer wavelength. Some fluorescent probes have been attached to genetic material and introduced into living organisms, making fluorescent probes a powerful method to obtain information about the structure, function, and health of cells.

The term "probe capable of fluorescing" as used herein means any compound, agent, substance, mixture, colloid, or biological material that is capable of fluorescing. In some embodiments, the probe may be delivered within the anatomy to an area where it may be caused to fluoresce. The following examples of probes capable of fluorescing are not to be construed as limiting. In one embodiment, the probe may be a mixture containing a fluorescence material, for example, a glucose solution mixed with fluoroscein. In another embodiment, the probe may be any type of colloid that is capable of fluorescing, for example, a fluorescent tagged sulfur colloid. In another embodiment, the probe may be a nanoparticle capable of fluorescing. The nanoparticle may be an inorganic nanoparticle, like a semiconductor nanocrystal, a silica-based nanoparticle, or any other inorganic particle capable of attaching to or containing a fluorescence material. The nanoparticle may be an organic nanoparticle, like a liposomal sphere, dimer structure, or other organic structures capable of attaching to or containing a fluorescence material. In another embodiment, the probe may be an antibody, such as a monoclonal antibody or a polyclonal antibody that is fluorescent tagged. The antibody may be any protein structure that may selectively attach to one or more locations on a biological cell or surface. In another embodiment, the probe may be a compound, substance, mixture, colloid, or biological material such as a peptide, nucleotide, liposome, an agent that targets vascular structures and/or deformities, or an anti-angiogenic drug that contains a fluorescent dye or has something capable of fluorescing attached thereto. In one embodiment, the probe may be a combination of any of the above probes. In another embodiment, the probe may include an agent that acts as a linking agent to bind the probe to a particular the anatomy or biomolecule.

In one embodiment, the probe may be a semiconductor nanoparticle. By use of the term "semiconductor nanoparticle" is meant any nanometer crystal or nanocrystal, cluster, nanosphere, nanorod, and/or nanocup of semiconductor compounds capable of emitting electromagnetic radiation upon excitation. In one embodiment, the semiconductor nanoparticle may instead be a nanostructure. A nanostructure is of a more intermediate size between molecular and microscopic structures. In some embodiments, the semiconductor compounds may come from Group II-VI and/or Group III-V elements. A semiconductor nanoparticle usually has a discrete quantized energy spectrum. The corresponding wave functions are spatially localized within the semiconductor nanoparticle, but extend over many periods of the crystal lattice. One of the optical features of small excitonic semiconductor nanoparticles immediately noticeable to the unaided eye is coloration. While the material which makes up the semiconductor nanoparticle defines its intrinsic energy signature, more significant in terms of coloration is the size.

The larger the semiconductor nanoparticle, the redder (the more towards the red end of the spectrum) the fluorescence.

In some embodiments, semiconductor nanoparticles may have the general formula MX, where X is selected from the group consisting of S, Se, or Te and resulting in the general formula MS, MSe, or MTe. Metal "M" may be Mg, Ca, Sr, Ba, Zn, Cd, and Hg as taught in U.S. Pat. No. 6,207,392 to Weiss et al. and U.S. Pat. No. 6,333,110 to Barbera-Guillem. In one embodiment, M is lead (Pb) and the resulting semiconductor nanoparticle may be PbS, PbSe, or PbTe. These lead based semiconductor nanoparticles have fluorescent wavelengths of about 700 to about 2500 nanometers (in the infrared range). PbS has a wavelength range of 850 to 2100 nm. PbSe has a wavelength range of 1200 to 2340 nm.

One commercially available semiconductor nanoparticle is PLxBead™ from Crystalplex Corp. (Pittsburgh, Pa.). The PLxBead™ semiconductor nanoparticle emit light for 30 minutes or more and can be produced in a variety of colors. Other semiconductor nanoparticles are available from Evident Technologies (Troy, N.Y.). Evident Technologies provides various semiconductor nanoparticle cores (CdSe, PbS, and PbSe) and core-shell arrangements (CdSe/ZnS) called EviDots™. They also provide EviTags™ semiconductor nanoparticles, which are functionalized semiconductor nanoparticles for biological applications. The EviTags™ semiconductor nanoparticles are functionalized with an amine or carboxyl terminal group.

Semiconductor nanoparticles may be tagged in numerous ways. The following examples of ways to tag semiconductor nanoparticles are merely representative and are not meant to be limiting. A bifunctional ligand can be used to link the semiconductor nanoparticle to a biomolecule. A TOPO-capped (trialkylphosphine oxide) semiconductor nanoparticle may be bound to a modified acrylic acid polymer by hydrophobic forces. Semiconductor nanoparticles may undergo silanization to attach to a biomolecule, which involves solubilization and bioconjugation of the semiconductor nanoparticle using a mercaptosilane compound. Semiconductor nanoparticles can be negatively charged and be electrostatically attracted to positively charged biomolecules. The semiconductor nanoparticles can be incorporated into microbeads and nanobeads that individually carry a "code" that targets specific biomolecules. For cancer cells, the semiconductor nanoparticles may be folate-conjugated, such that the semiconductor nanoparticle can bind to the folic acid inside cancer cells. Additionally, semiconductor nanoparticles can be "functionalized," as explained in U.S. Pat. No. 6,333,110, so that the semiconductor nanoparticle will contact and bind with living the anatomy.

In another embodiment, the probe may be a silica-based nanoparticle. By use of the term "silica-based nanoparticle" is meant any nanoparticle consisting of a core containing photoluminescent dye molecules surrounded by a protective silica shell. The silica-based nanoparticles are commonly known as Cornell dots or CU dots. The silica-based nanoparticles may be used in place of a semiconductor nanoparticle or nanostructure in any of the applications disclosed herein. Silica-based nanoparticles are described in U.S. Published Patent Applications 2004/0101822 to Wiesner et al., 2006/0183246 to Wiesner et al., and 2006/0245971 to Burns et al., which are hereby incorporated by reference in their entirety.

In another embodiment of the system, the probe may be a fluorescent tagged monoclonal antibodies or fragments of a monoclonal antibodies. Monoclonal antibodies are antibodies that are identical because they were produced by one type of immune cell and are clones of a single parent cell. Given (almost) any substance, it is possible to create monoclonal antibodies that specifically bind to that substance. The mAb can then serve to detect or purify that substance. For example mAb can be developed that are immunofluorescence test monoclonal antibodies (fluorescent tagged mAb) that bind only to cancer cell-specific antigens. Some fluorescent tagged mAb may even induce an immunological response against the target cancer cell.

In one embodiment, the fluorescent tagged mAb is injected into the area of the anatomy to be examined. The area of the anatomy may be the colon, rectum, gastrointestinal tract, esophagus, or any region in the body where there are cancerous cells or a cancerous lumps. The fluorescent tagged mAb after binding to the cancer cells and being exposed to the fluorescence excitation beam of radiation will emit a fluorescence wavelength(s) that is then detected and displayed on the image display system. The image showing the location of the fluorescence on or within the area of the anatomy indicates to a surgeon where the cancerous cells are located, so that the cancerous cells can all be removed during surgery. This technique is an improvement in visualizing the cancerous cells in the anatomy, which includes the surrounding the anatomy, lymph nodes, etc., surrounding the main cancer source (i.e. a lump or tumor). The anatomy surrounding the main cancer source is called the "margin." The assembly 200 detects fluorescence of the fluorescent tagged mAb and may be capable of margin identification of cancer cells during colorectal cancer resection, a lumpectomy, or in diagnosing various cancers in the gastrointestinal tract, like Barrett's esophagus. To visualize the esophagus a flexible endoscope embodiment of the present invention is passed through the mouth to examine the esophagus, stomach and the first part of the small intestine called the duodenum.

In another embodiment of the system for examining an area of a patient's anatomy, the fluorescent probe is a fluorescent tagged sulfur colloid (FTSC). The fluorescent tag may be a semiconductor nanoparticle, a silica-based nanoparticle, or any other fluorescence marker that may be combined with or tagged onto the sulfur colloid to make the sulfur colloid capable of fluorescing. The FTSC may be injected into an area of the anatomy where cancer originated. The FTSC will be carried by the lymphatic vessels to the sentinel lymph node where cancer cells are likely to have spread. The sentinel lymph node is the first node, or group of nodes, in the body to come into contact with cancer cells that have left the original cancer location and started to spread. For example, the usual location for the sentinel lymph nodes in breast cancer is under the arm. The FTSC can then be exposed to an excitation wavelength from an excitation source using the assembly 200 (described below) or embodiments thereof, so that the sentinel lymph nodes will be fluorescently imaged on the display system. A surgeon may then surgically remove, ablate, or treat the sentinel lymph nodes.

In one embodiment, the scanning beam assembly, described below, may be used to excite naturally occurring autofluorescent biomolecules within the anatomy. Autofluorescence may occur in endogenous cell constituents such as, but not limited to, NADH, riboflavin and flavin coenzymes.

The term "fluorescence image" as used herein means the visual representation of the radiation from the fluorescence of the probe or autofluorescent molecule. The fluorescence image may be formed from the intensity pattern of fluorescence given off by an excited probe or autofluorescent molecule. Fluorescence results in radiation of a different wavelength than the wavelength of necessary excitation radiation.

The term "reflectance image" as used herein means the visual representation of the field-of-view or anatomy derived from all other radiation (not the fluorescence) returned from the FOV. The returned radiation is the result of the other wavelengths of radiation interacting with the FOV (i.e., reflecting, refracting, scattering, absorbing). The fluorescence image and the reflectance image may be displayed together in anatomical registrations, such that the location of the fluorescence on the anatomy is displayed.

Figure 2A:
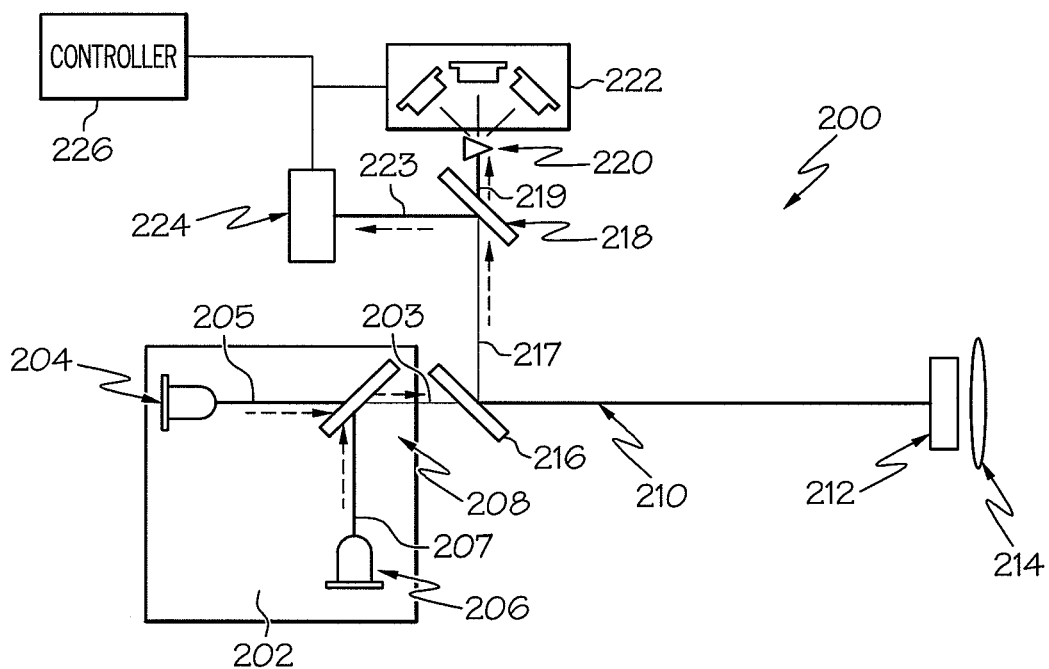
FIGS. 2A and 2B are block diagrams of embodiments of a scanning beam assembly including a fluorescence detector.
Figure 2B:
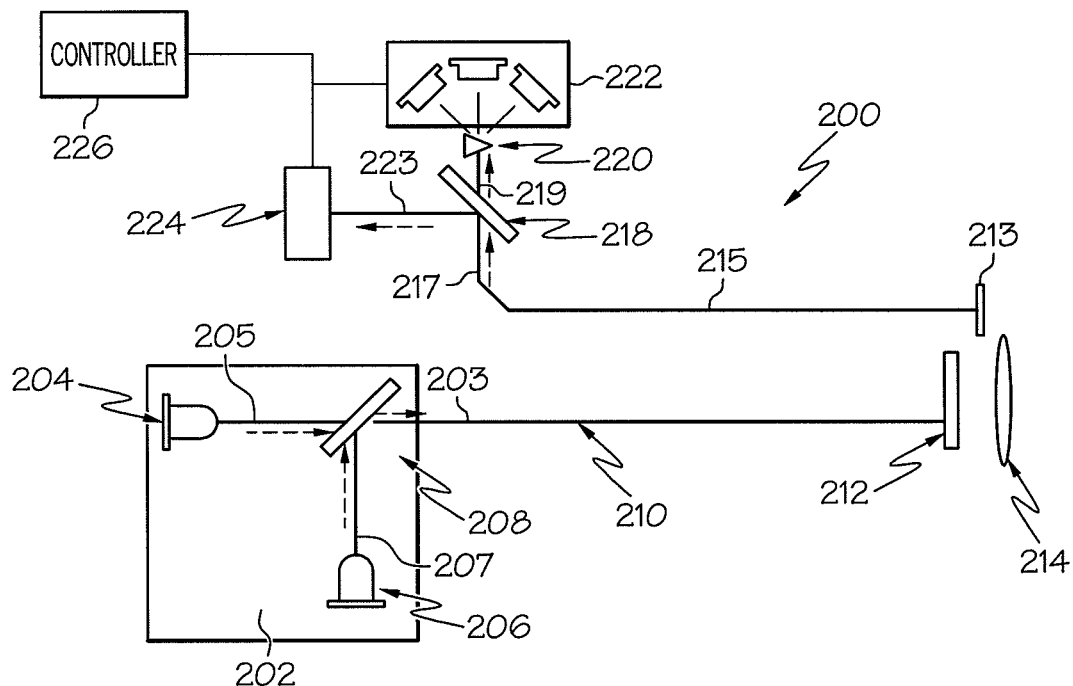

Referring now to FIGS. 2A and 2B, scanning beam assembly 200 is illustrated as including radiation source 202 for emitting a beam of radiation 203, scanning device 212, imaging detector 222, fluorescence detector 224, and controller 226. Radiation source 202 may contain at least one imaging source 204 and at least one fluorescence excitation source 206. Other embodiments for radiation source 202 are disclosed in commonly assigned U.S. patent application Ser. No. 11/716,806 MEDICAL DEVICE INCLUDING SCANNED BEAM UNIT FOR IMAGING, THERAPY, AND/OR DIAGNOSIS, which is hereby incorporated by reference in its entirety. Radiation emitted from imaging source 204 is shown as imaging radiation 205. Fluorescence excitation source 206 emits excitation radiation 207. In some embodiments, imaging radiation 205 and excitation radiation 207 may be combined by combiner 208. Beam combiner 208 combines these sources of radiation into a single beam of radiation 203, which travels through optical fiber 210 to the scanning device 212.

In one embodiment, the beam of radiation 203 hits partially-reflective lens 214, the radiation is reflected back toward optical fiber 210 onto the scanning device 212. In one embodiment, scanning device 212 may be a MEMS oscillating reflector. The MEMS type reflector may oscillate in at least two directions to scan the field-of-view (FOV). The MEMS reflector then directs the radiation 203 out onto the FOV. The FOV will return some of radiation 203 back toward lens 214 (i.e., as reflected, absorbed, scattered, and/or refracted radiation) along with fluorescence radiation from a probe within the FOV that may be excited by the fluorescence excitation radiation 207.

In one embodiment, scanning device 212 may be a point source from a single optical fiber that can be scanned using a small metal cantilever driven in vibratory mechanical resonance. In another embodiment, a two-dimensional scanner may include a quartz mechanical resonator or micro-optical scanner to drive the optical fiber itself. The scanning fiber may be driven by a piezo electric 2D actuator in an amplitude-modulated circular pattern or spiral pattern.

In another embodiment, scanning device 212 may include a moving lens. The moving lens may be any suitable refracting device that is capable of directing the radiation from the radiation source onto the FOV.

In one embodiment, as shown in FIG. 2A, radiation returned from the field of view is collected at lens 214 by collectors and transmitted back up optical fiber 210. The returned radiation is deflected by mirror 216. Returned radiation 217 is directed toward imaging detector 222 and the fluorescence detector 224. The beam of returned radiation 217 may enter splitter 218 to be separated into returned imaging radiation 219 and fluorescence 223 emitted from a probe or probes capable of fluorescing.

In another embodiment, as shown in FIG. 2B, radiation returned from the field of view is collected at lens 214 by collector 213 and transmitted by return fiber 215 to beam splitter 218. Return fiber 215 bypasses mirror 216 in this embodiment.

Figure 3:
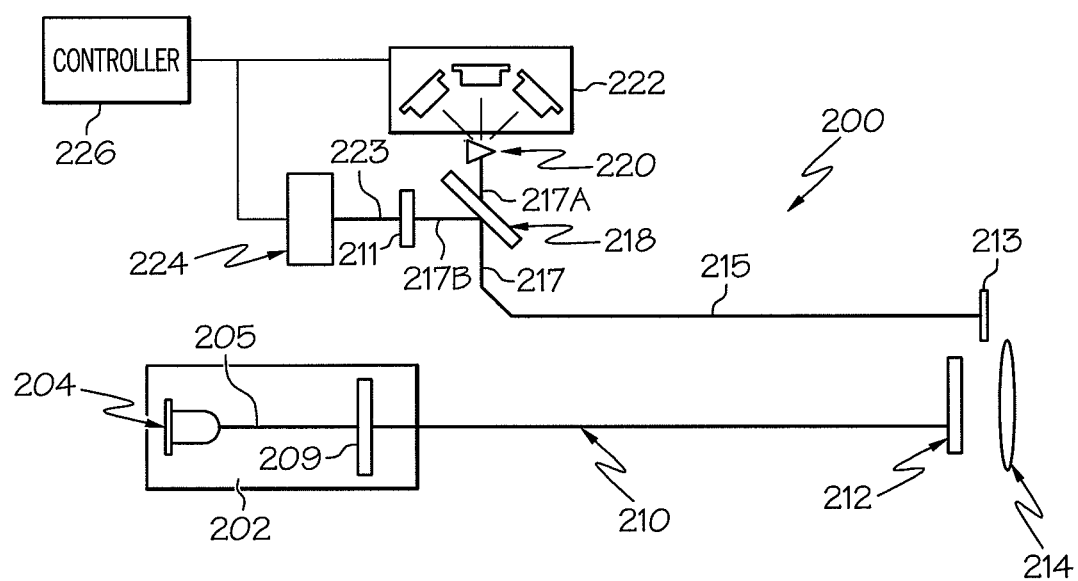
FIG. 3 is a block diagram of another embodiment of the scanning beam assembly.

Fluorescence detector 224, in FIGS. 2A, 2B and 3, may be a spectrometer tunable to various wavelengths that correspond to fluorescence wavelength(s) of a chosen probe. The spectrometer may be tunable to several wavelengths at once or at separate times, allowing for the use of a plurality of probes within the same area of the anatomy. In another embodiment assembly 200 may include a plurality of spectrometers set at various wavelengths. Some probes emit weak or strong fluorescence radiation in the visible range, others may emit radiation outside the visible range, and yet other probes may have a combination thereof. For probes with stronger emissions outside the visible range the spectrometer may be used to detect the stronger wavelengths. The spectrometer may filter the wavelengths to a narrower band of wavelengths to increase the frequency or wavelength sensitivity of the system. The spectrometer's wavelength selection capacity may also be used to select and detect weak wavelengths in the visible range. If a probe emits strongly in the visible range, the photodetectors 222 may be used to detect the fluorescence.

In another embodiment, fluorescence detector 224 may be a filter that detects a particular fluorescence wavelength. In another embodiment, fluorescence detector 224 may include a plurality of filters, where one filter may be selected to be placed into the fluorescence detector position at a time.

The returned imaging radiation 219 is separated into various wavelengths by a separator 220 selected to separate the radiation into a plurality of desired wavelengths. The separate wavelengths are then directed to the appropriate detectors within photodetector 222. The fluorescence 223 is directed to fluorescence detector 224. Fluorescence detector 224 and photodetector 222 convert the fluorescence and returned imaging radiation into signals to be transmitted to controller 226. Controller 226 converts the signals into displayable images for both the fluorescence and the FOV. Controller 226 will create a fluorescence image that may be displayed within the color scheme of a display system so that the fluorescence image may be registered within the image of the FOV. In some embodiments, the wavelengths of the fluorescence are outside the visible range, so controller 226 converts the fluorescence signal into a fluorescence designated color that is within the color scheme of the display system. In other embodiments, the wavelength of the fluorescence may be within the wavelengths of the imaging source and radiation from the imaging source that was returned from the field of view. Separate photodetectors, like 222, may be used to detect the fluorescence 223 and the returned imaging radiation 219. The controller 226, in this embodiment, generates a fluorescence signal from the fluorescence 223 and keeps it separate from the signals generated from the returned imaging radiation 219, and converts the fluorescence signal into a fluorescence designated color within the color scheme of the display system so that the fluorescence stands out on the image of the rest of the field-of-view. The resulting image is significantly improved in spectral efficiency and performance over systems that do not employ probes. The image may be displayed on a display system for the user to examine the area within the anatomy that now has a portion of the area shown as containing the fluorescence of the probe.

Optical fiber 210 may be rigid or flexible, which makes the fiber 210 adaptable for use with endoscopes, laparoscopes, catheters, or any other medical scope. Optical fiber 210 allows for the delivery of a large amount of imaging or excitation radiation to a single pixel detection system and only requires a low-power source. The use of a single pixel detector allows the detection area to be in excess of $10^7$ $\mu m^2$, which will increase the photosensitivity and reduce the imager's noise intensity.

Referring now to FIG. 3, in another embodiment, scanning beam assembly 200 is illustrated as including radiation source 202, first filter 209, second filter 211, scanning device 212, imaging detector 222, fluorescence detector 224, and controller 226. Radiation source 202 may contain at least one imaging source 204 that emits imaging radiation 205 that may be capable of emitting a fluorescence excitation wavelength within the imaging radiation wavelengths. Imaging radiation 205 may be filtered by first filter 209 to remove the wavelength(s) from the imaging radiation that are within the range of the expected fluorescence wavelengths from the probe. For example, if a probe fluoresces at a wavelength of about 530 nm, then first filter 209 will remove wavelengths of about 530 nm from imaging radiation 205, so that any detection of wavelengths of about 530 nm will be known to be from the probe's fluorescence. The filtered radiation travels through optical fiber 210 to the scanning device 212, out onto the FOV, and some of the filtered radiation returns from the FOV along with fluorescence wavelengths from a probe that was delivered to the FOV.

Returned radiation 217 may be directed toward splitter 218. Returned radiation 217A may be separated by separator 220 before entering photodetector 222. Returned radiation 217B may be filtered by a second filter 211 to remove all wavelengths except the wavelengths within the range of expected fluorescence wavelengths. The expected fluorescence wavelengths pass through the filter as fluorescence beam 223. Fluorescence 223 may be detected by fluorescence detector 224, which may be any of the fluorescence detectors described above. In another embodiment, fluorescence detector 224 may be a photodetector, like photodetector 222. Photodetector 222, fluorescence detector 224, and controller 226 are described above in more detail.

In one embodiment, the system further includes a display system for displaying an image of the fluorescence within the field-of-view. The display system may be any type of screen that will effectively show the area of the anatomy and the location(s) in or on the anatomy where the probe is emitting fluorescence, i.e. the fluorescence is anatomically registered with the visual image of the area of the anatomy being examined. In one embodiment the display system may be a monitor that receives the output from the scanning beam assembly's controller. In one embodiment the display system may include a recording medium and a digitizer.

In certain embodiments, at least part of the scanning beam assembly may be included in a medical instrument. The medical instrument may include scanning device 212, collector 213, optical fiber 210, lens 214, and any other components necessary to make the reflector scan the field-of-view. The medical instrument may be insertable within the anatomy to scan the anatomy with a beam of radiation that excites the probe and detects the probe's fluorescence. The insertable portion of the medical instrument may be a rigid or flexible. The medical instrument may be an endoscope, laparoscope, catheter, surgical stapler, surgical clamp, surgical grasper, trocar, needle or any other medical scope, tool, or device adapted to scan the anatomy with a beam of radiation. In other embodiments, the scanning portion that is insertable into the anatomy may be housed within a deployable scanning beam unit or scanning module as disclosed in U.S. patent application Ser. No. 11/651,255 METHOD OF IN VIVO MONITORING USING AN IMAGING SYSTEM INCLUDING SCANNED BEAM IMAGING UNIT, which is herein incorporated by reference in its entirety.

In some embodiments, the probe may be delivered to an area within a patient's anatomy. The area within the anatomy may be a tumor, a cancer site, a lumen, an organ, the blood stream, the lymphatic system, or any other particular area of the anatomy to be imaged using fluorescence. Any conventional or known method for delivering the probe can be used, although, intravenous injection is most common. In one embodiment, the probe may be contained in an injectable suspension.

In another embodiment, the medical instrument may be coated with a fluorophore. The fluorophore may be any of the above listed compounds or substances capable of fluorescing. The instrument may be any medical instrument that is to be inserted within the anatomy during a procedure. The instrument may be introduced intralumenally in an open and/or laparoscopic procedure, into a body cavity, or other body the anatomy. In other embodiments, the fluorophore may be part of a housing covering the instrument, or part of the material making up a piece of the instrument itself. In some embodiments, the housing may be a plastic containing the fluorophore. In other embodiments, the tip of the instrument includes the fluorophore.

The fluorophore contained on or within the material of the instrument may then be excited by an excitation wavelength to cause the fluorophore to fluoresce. The fluorescence may be visible to the naked eye, visualized using the assembly described above, or both. In some embodiments, the reflector that is directing the beam of radiation onto the field of view including the instrument containing the fluorophore may be within the same location as the instrument, while in other embodiments the reflector may be external to the lumen or area of the body where the instrument is located. If the reflector is external to the lumen, then the source may need to emit longer wavelengths of radiation to penetrate through the anatomy, so the excitation radiation can reach the fluorophore and cause it to fluoresce. The radiation may be near infrared or longer wavelengths. In one embodiment, the fluorophore may be a semiconductor nanocrystal within the material on or in the instrument, or a coating on the instrument. The fluorophore while fluorescing enables the visualization of the movement of the instrument as it is routed through the lumen, body cavity, or other the anatomy.

In another aspect, the present invention provides a method for observing fluorescence within an area of a patient's body that comprises delivering a probe capable of fluorescing into a patient's anatomy, introducing at least part of a scanning beam assembly into the anatomy to scan the area of the anatomy including the probe, exciting the probe, detecting the probe's fluorescence, and converting the probe's fluorescence into a displayable image of the fluorescence within the area of the anatomy including the probe. The scanning beam assembly comprises a radiation source capable of emitting one or more wavelengths of radiation that are capable of exciting the probe and causing the probe to fluoresce, a reflector that receives the radiation from the radiation source to direct the radiation onto the area of the anatomy, wherein the reflector oscillates in at least two directions to create a scan of the area of the anatomy, at least one detector to detect radiation returned from the area of the anatomy, and a controller to convert the detected radiation into a displayable image of the fluorescence within the area of the anatomy. The observed fluorescence may enable the examination, diagnosis, treatment, or visualization of the area of the anatomy that includes the probe.

The probe may be delivered by any of the methods mentioned above, but is not limited thereto. The instrument may be introduced transorally, transanally, translumenally, or through a trocar. The beam of radiation is emitted as described above through an optical pathway, usually an optical fiber bundle. The probe's fluorescence may be detected by a specialized fluorescence detector, or if the fluorescence is in the visible range a photodetector may be used. In one embodiment, the detector is a spectrometer, which may be included in an assembly 200 like that illustrated in FIG. 2. The fluorescence may be displayed using a display systems.

In one embodiment, the method may be used during a surgical procedure to visualize part(s) of the anatomy near a surgery site. The visualization may protect the visualized parts of the anatomy from being compromised during the surgical procedure. For example, to protect the biliary tree from bile duct compromise during a cholecystectomy a probe capable of fluorescing may be injected into the biliary tree. The visualization of the biliary tree should decrease the occurrence of bile duct compromise during surgery. The probe may then be excited and the probe's fluorescence detected using the scanning assembly 200. Assembly 200 converts the detected fluorescence using controller 226 into an image that can be displayed. This image may then be displayed on a display system so a surgeon can see where the biliary tree is during the procedure. In one embodiment, the surgical instrument being used may include a fluorophore so the surgeon can determine where the instrument is in relation to the fluorescing biliary tree. The probe may be any of the probes listed above. In one embodiment, the probe may be a nanoparticle, such as a semiconductor nanocrystal. The semiconductor nanocrystal provides orders of magnitude greater light emission and has a wide separation between the excitation wavelength and the fluorescence emission wavelength, so little filtering of the wavelengths is needed.

In another embodiment, the method may be used to determine the extent, margin, or outer limits of a specific structure. For example, but not limited thereto, a fluorescence probe may be used to visualize the extent of the diseased or compromised the anatomy around a benign or cancerous legion (tumor) such that a surgeon may reliably remove a clinically relevant 'margin' of the anatomy around the diseased or compromised the anatomy.

In one embodiment, the semiconductor nanocrystal is one of the lead based semiconductor nanoparticles, PbS, PbSe, or PbTe. The semiconductor nanoparticles are suspended in an injectable form that may be intralumenally injected into the biliary tree. The excitation wavelength for PbS, PbSe, or PbTe may be tailored to the infrared spectrum. The excitation wavelength may be between about 700-2500 nm. These wavelengths allow the excitation radiation to penetrate deeper into the anatomy (i.e., the biliary tree) than shorter wavelengths, thus causing the semiconductor nanocrystals to fluoresce. The fluorescence is detected, converted, and displayed for the doctor to visualize the biliary tree during the cholecystectomy and avoid bile duct compromise.

In another embodiment, the method may be used during colorectal or gynecological procedures to visualize at least one of the kidneys, ureters, urethra, and bladder to protect them from being compromised. The probe may be contained within an intravenous solution that may be injected (i.e., intravenously) into the bloodstream. The solution containing the probe will pass through the bloodstream to the kidneys where the kidneys will clear the probe from the bloodstream. The probe may remain in the kidneys for fluorescence visualization, or may be flushed from the kidneys into the ureters, the bladder, and out the urethra. Some of the probe may remain in each of the kidneys, ureter, bladder, and urethra allowing for the visualization of them all at once. In other embodiments, a probe that is selective to one of the kidneys, ureter, bladder, or urethra may be used.

In another embodiment of the present invention, a method of examining an area of a patient's anatomy and an instrument that comprises delivering a probe capable of fluorescing to a the anatomy; introducing an instrument containing at least in part a fluorophore; exposing the probe, fluorophore, or both to a radiation source or sources that emits one or more wavelengths of radiation capable of exciting the probe, fluorophore, or both into fluorescing; detecting fluorescence of the probe, fluorophore, or both; converting the detected fluorescence into an image that can be displayed; and displaying the fluorescence on a display system that is capable of displaying an image of the anatomy and the instrument. In one embodiment, the instrument is introduced into the colon or other parts of the gastrointestinal track. An instrument containing a fluorophore gives the user the advantage of knowing the location of the instrument (i.e., a colonoscope if in the colon) as it moves along the length of the lumen (i.e., the colon).

The probe may be delivered to the anatomy by any of the ways disclosed above. In one embodiment, the fluorophore is included in a coating on the instrument. In another embodiment the fluorophore is included in a housing that covers the instrument. In yet another embodiment, the fluorophore is included in material that the instrument is made of. The fluorophore may be included in any part of the instrument, preferably the tip of the instrument.

The probe and fluorophore may be any of the above listed compounds or substances capable of fluorescing. In one embodiment, the probe and fluorophore may be selected from fluorescent tagged monoclonal antibodies, semiconductor nanocrystals, fluorescent tagged sulfur colloids, fluorescent dyes, or combinations thereof. In some embodiments, the probe and fluorophore may be the same, while in other embodiments they may be different.

In one embodiment, the radiation source may be any of the fluorescent excitation sources described above, and may be included in a scanning beam assembly similar to the assembly 200 shown in FIG. 2. The radiation source may emit one or more wavelengths of radiation that are capable of exciting the probe, fluorophore, or both. In one embodiment, one wavelength may excite both the probe and fluorophore, while in other embodiments the probe and fluorophore may be excited by different wavelengths. In one embodiment, the probe and fluorophore may be excited by different wavelengths at the same time, while in other embodiments it may be advantageous to excite one probe at a time.

In one embodiment, the scanning beam assembly is separate from the instrument and is introduced into the anatomy to scan the field-of-view with excitation wavelengths. The scanning of the beam will expose the probe and fluorophore to the excitation wavelengths and cause the probes to fluoresce. The scanning beam assembly includes a radiation source capable of directing the radiation onto at least one reflector that oscillates in at least two directions to create a scan of a field-of-view, at least one detector to detect radiation returned from the field-of-view, and a controller to convert the detected radiation into a signal indicative of the field-of-view including the fluorescence. In one embodiment, the scanning beam assembly may be placed relative to, but outside the site within the anatomy where the probe and fluorophore are to be visualized. Then using wavelengths of radiation that are capable of penetrating the site within the anatomy as the excitation radiation, the excitation radiation will travel through the nearby anatomy and excite the probe and fluorophore, causing them to fluoresce. In some embodiments, infrared radiation may be needed to penetrate the anatomy, however, in other embodiments when the anatomy is thinner, like a blood vessel, green wavelengths of radiation may be enough to penetrate the anatomy to excite the probe or fluorophore. In some embodiments the fluorescence given off by the probe, fluorophore, or both may be visible with the naked eye. If the fluorescence is to be displayed on a display system, then the fluorescence given off may need to be of a long enough wavelength to travel back through the anatomy to reach the detectors of the scanning beam assembly. In another embodiment, a detector may be included in the instrument, and may be connected to the scanning beam assembly's controller using an optical fiber or connected to some other controller and display system.

In another embodiment, the instrument containing the fluorophore also includes at least part of a scanning beam assembly to scan the area of the anatomy that includes the probe and instrument's fluorophore. The scanning beam assembly is described above in more detail.

While the present invention has been illustrated by description of several embodiments, it is not the intention of the applicant to restrict or limit the spirit and scope of the appended claims to such detail. Numerous other variations, changes, and substitutions will occur to those skilled in the art without departing from the scope of the invention. For instance, the device and method of the present invention has been illustrated in relation to examining and imaging fluorescence in the anatomy, but it will be understood the present invention has applicability to fluorescent imaging in other materials. Moreover, the structure of each element associated with the present invention can be alternatively described as a means for providing the function performed by the element. It will be understood that the foregoing description is provided by way of example, and that other modifications may occur to those skilled in the art without departing from the scope and spirit of the appended Claims.

What is claimed:

1. A system for examining an area of a patient's anatomy comprising:
   a) a probe capable of fluorescing, the probe configured to be deliverable within the anatomy; and
   b) a medical instrument including at least part of a scanning beam assembly and having an outer surface that includes, at least in part, a fluorophore, wherein the scanning beam assembly scans the probe with a beam comprising imaging radiation and excitation radiation and detects the probe's fluorescence while simultaneously detecting imaging radiation returned from a field-of-view, the scanning beam assembly comprising:
      a radiation source configured for simultaneously emitting one or more wavelengths of imaging radiation and excitation radiation, the excitation radiation being configured for exciting the probe and the fluorophore and causing the probe and the fluorophore to fluoresce;
      a scanning device that includes an oscillating reflector that directs the imaging and excitation radiation onto the field-of-view to create a scan of the field-of-view;
      a separator that separates radiation returned from the field-of-view into imaging radiation and fluorescence radiation;
      a first detector configured to detect the imaging radiation and a second detector configured to detect the fluorescence radiation; and
      a controller configured to convert the detected imaging radiation into a displayable image of the field-of-view and the detected fluorescence radiation into a displayable fluorescence image of both the probe and the fluorophore;
   wherein the fluorophore while fluorescing enables the visualization of the movement of the outer surface of the instrument.

2. The system of claim 1 further comprising a display system for displaying the image of the field-of-view and the fluorescence image.

3. The system of claim 2 wherein the fluorescence image of the probe is anatomically registered with the image of the field-of-view.

4. The system of claim 2 wherein the controller converts the fluorescence radiation into a fluorescence designated color that is within a color scheme of the display system such that the fluorescence stands out on the image of the field-of-view.

5. The system of claim 1 wherein the probe is selected from the group consisting of a nanoparticles, antibody, colloid, dye, mixture, substance or combinations thereof that are capable of fluorescing.

6. The system of claim 5 wherein the probe is configured to be delivered within the patient's anatomy to a tumor, a cancer site, a lumen, an organ, or blood stream.

7. The system of claim 5 wherein the probe is an injectable solution delivered to the blood stream to be cleared by the kidneys so the probe is distributed within at least one of the kidneys, ureters, bladder, and urethra.

8. The system of claim 5 wherein the nanoparticles is a semiconductor nanoparticles, a silica-based nanoparticle, or mixtures thereof.

9. The system of claim 5 wherein the antibody is a fluorescent tagged monoclonal antibody.

10. The system of claim 1 wherein the second detector is a spectrometer or a filter.

11. The system of claim 10 wherein the second detector is a tunable spectrometer that is tunable to various wavelengths including at least one fluorescence wavelength of the probe.

12. The system of claim 1 wherein the fluorophore is a nanoparticle, colloid, dye, substance, mixture, or combination thereof that are capable of fluorescing.

13. The system of claim 1 wherein the fluorophore is a part of a housing covering the instrument, a coating on the instrument, or a part of the instrument itself.

14. A method for observing fluorescence within an area of a patient's anatomy comprising:
   delivering a probe capable of fluorescing into a patient's anatomy;
   introducing an instrument into the anatomy to scan the area of the anatomy that includes the probe, wherein the instrument includes at least part of a scanning beam assembly and has an outer surface that includes a fluorophore, the scanning beam assembly comprising:
      a radiation source configured for simultaneously emitting one or more wavelengths of imaging radiation and excitation radiation, the excitation radiation being capable of exciting the probe and the fluorophore and causing the probe and the fluorophore to fluoresce;
      a scanning device that directs the imaging and excitation radiation onto the area of the anatomy to create a scan of the area;
      a separator that separates radiation returned from the area of the anatomy into imaging radiation and fluorescence radiation;
      a first detector configured to detect the imaging radiation and a second detector configured to detect the fluorescence radiation; and
      a controller configured to convert the detected imaging and fluorescence radiation into a displayable image of the anatomy that includes a fluorescence image;
   scanning the area of the anatomy that includes the probe and at least a portion of the medical instrument that includes the fluorophore with imaging radiation and excitation radiation;
   detecting the probe's fluorescence with the second detector;

converting the probe's fluorescence into a displayable fluorescence image;
detecting the fluorescence of the fluorophore with the second detector;
converting the detected fluorescence of the fluorophore into a fluorescence image of the outer surface of the portion of the instrument comprising the fluorophore;
detecting the imaging radiation returned from the anatomy with the first detector;
converting the imaging radiation returned from the anatomy into an image of the anatomy; and
displaying the fluorescence image of the outer surface of the instrument on a display system combined with the fluorescence image of the probe and the image of the anatomy.

15. The method of claim 14 further comprising displaying the fluorescence image of the probe in anatomical registration with the image of the anatomy.

16. The method of claim 15 wherein the controller converts the fluorescence radiation into a fluorescence designated color that is within a color scheme of the display system such that the fluorescence stands out on the image of the anatomy.

17. The method of claim 14 wherein the probe is selected from the group consisting of a nanoparticle, antibody, colloid, dye, mixture, substance or combinations thereof that are capable of fluorescing.

18. The method of claim 17 wherein the nanoparticle is a semiconductor nanoparticle, a silica-based nanoparticle, or mixtures thereof.

19. The method of claim 17 wherein the antibody is a fluorescent tagged monoclonal antibody.

20. The method of claim 17 wherein the probe is delivered within the patient's anatomy to a tumor, a cancer site, a lumen, an organ, or blood stream.

21. The method of claim 17 wherein the probe is an injectable solution delivered to the blood stream to be cleared by the kidneys to distribute the probe within at least one of the kidneys, ureters, bladder, and urethra for fluorescence observation during a colorectal or gynecological procedure.

22. The method of claim 17 wherein the probe is injected into a biliary tree for fluorescence observation during a cholecystectomy.

23. The method of claim 14 wherein the second detector is a spectrometer or a filter.

24. The method of claim 23 wherein the second detector is a tunable spectrometer that is tunable to various wavelengths including at least one fluorescence wavelength of the probe.

25. The method of claim 14 wherein the fluorophore is selected from the group consisting of a nanoparticle, antibody, colloid, dye, mixture, substance and combinations thereof that are capable of fluorescing.

26. The method of claim 25 wherein the nanoparticle is a semiconductor nanoparticle, a silica-based nanoparticle, or mixtures thereof.

27. The method of claim 25 wherein the antibody is a fluorescent tagged monoclonal antibody.

28. A method for examining an area of a patient's anatomy comprising:
introducing a medical instrument into the anatomy to scan the anatomy, wherein the medical instrument has an outer surface that includes, at least in part, a fluorophore and includes at least part of a scanning beam assembly;
the scanning beam assembly comprising:
a radiation source configured for simultaneously emitting one or more wavelengths of imaging radiation and excitation radiation, the excitation radiation being capable of exciting a naturally occurring autofluorescent cell constituent and the fluorophore;
a scanning device that directs the imaging and excitation radiation onto a field-of-view to create a scan of the field-of-view, the scanning device including a reflector that receives both the imaging and the excitation radiation from the radiation source onto the anatomy, wherein the reflector oscillates in at least two directions to create a scan of the anatomy with both the imaging and excitation radiation;
a separator that separates radiation returned from the field-of-view into imaging radiation and fluorescence radiation;
a first detector configured to detect the imaging radiation and a second detector configured to detect the fluorescence radiation; and
a controller configured to convert the detected imaging and fluorescence radiation into a displayable image of the anatomy that includes a fluorescence image;
scanning the area of the anatomy that includes the autofluorescent cell constituent and at least a portion of the medical instrument that includes the fluorophore with at least the excitation radiation;
detecting the fluorescence of the autofluorescent cell constituent with the second detector; and
converting the fluorescence into a displayable fluorescence image of the autofluorescent cell constituent;
detecting the fluorescence of the fluorophore with the second detector;
converting the detected fluorescence of the fluorophore into a fluorescence image of the outer surface of the portion of the instrument having the fluorophore;
detecting the imaging radiation returned from the anatomy with the first detector;
converting the imaging radiation returned from the anatomy into an image of the anatomy; and
displaying the fluorescence image of the outer surface of the instrument on a display system combined with the fluorescence image of the autofluorescent cell constituent and the image of the anatomy;
wherein the second detector is a tunable spectrometer that is tunable to various wavelengths including at least one fluorescence wavelength of the autofluorescent cell constituent.

29. The method of claim 28 further comprising displaying the fluorescence image of the autofluorescent constituent in anatomical registration with the image of the anatomy.

* * * * *